United States Patent [19]

Itay

[11] Patent Number: 5,053,050
[45] Date of Patent: Oct. 1, 1991

[54] COMPOSITIONS FOR REPAIR OF CARTILAGE AND BONE

[76] Inventor: Samuel Itay, 16/3 Sharet St., Kfar-Saba, Israel, 44456

[21] Appl. No.: 187,730

[22] Filed: Apr. 29, 1988

[51] Int. Cl.$^5$ .............................................. A61F 2/28
[52] U.S. Cl. ........................................ 623/16; 623/66
[58] Field of Search .................................... 623/16, 66

[56] References Cited

U.S. PATENT DOCUMENTS 4,481,946  11/1984  Altshuler et al.
4,486,188  12/1984  Altshuler et al.
4,642,120   2/1987  Nevo et al. ............................ 623/16
4,721,096   1/1988  Naughton et al.

OTHER PUBLICATIONS

S. Itay et al., "Use of Cultured Chick Epiphyseal Chondrocytes as Grafts for Defects in Chick Articular Cartilage", *Clinical Orthopedics*, pp. 284–303, Jul., 1987.
Bentley, G. et al., "Homotransplantation of Isolated Epiphyseal and Articular Cartilage Chondrocytes into Joint Surfaces of Rabbits", *Nature* 230, pp. 385–388, Apr. 9, 1971.
Bentley, G. et al., "Isolated Epiphyseal Chondrocyte Allographs into Joint Surfaces—An Experimental Study in Rabbits", *Annuals Rheumatic Diseases*, 37, pp. 449–458 (1978).
Helbing, G. et al., "In-vitro—Untersuchungen an Isolierten Chondrozyten zur Prognose von Knorpeltransplantaten", *Helv. Chir. Acta* 46, pp. 21–24 (1979).
Urist, Marshall R. et al., "Bone Cell Differentiation and Growth Factors", *Science*, vol. 220, pp. 680–686, May 13, 1983.
Urist, Marshall R. et al., "Cartilage or Bone Induction by Articular Cartilage", *The Journal of Bone and Joint Surgery*, vol. 50B, No. 1, pp. 198–215, Feb. 1968.
Chesterman, P. J. et al., "Homotransplantation of Articular Cartilage and Isolated Chondrocytes", *The Journal of Bone and Joint Surgery*, vol. 50B, No. 1, pp. 184–197, Feb. 1968.
Aprahamian, Marc et al., "A New Reconstituted Connective Tissue Matrix: Preparation Biochemical Structural and Mechanical Studies", *Journal of Biomedical Materials Research*, vol. 21, pp. 965–977 (1987).

*Primary Examiner*—David J. Isabella
*Attorney, Agent, or Firm*—Merchant, Gould, Smith, Edell, Welter & Schmidt

[57] ABSTRACT

A defect is provided in cartilage or bone, or both, to excize damaged or pathological tissue, and it is filled with an implant having capability for complete regeneration of the skeletal tissue as a chondrogenic or osteogenic phenotype. The implant comprises cells expressing a chondrocyte phenotype ($80 \times 10^6$ cells/ml) embedded in a biocompatible matrix having about 20% serum, which provides a permissive environment for maturation and transformation of the implant to a fully integrated state with the surrounding tissue. A portion of the implant may comprise a bone segment or a bone substitute.

1 Claim, No Drawings

COMPOSITIONS FOR REPAIR OF CARTILAGE AND BONE

BACKGROUND OF THE INVENTION

U.S. Pat. No. 4,642,120, of which I am a co-inventor, describes compositions for use in repairing bone and cartilage by implantation of material comprising a proliferating chondrocyte cell structure having phenotypic capability embedded in a vehicle or gel consisting of thrombin, antiprotease, fibrinogen, extracellular matrix and one or more growth factors that forms a "biological glue" of a biodegradable character. Before implantation the cells are grown in a tissue culture and harvested, and the chondrocyte population is embedded in the biological glue at a concentration of between from 100,000 to 500,000 cells per milliliter of glue. Before using this formulation, damaged cartilage and bone, as in a hip or other joint, are excised by surgery. A matching implant of the formulation is then inserted in the cavity, with or without bone segments to fill part of the volume. Cell proliferation continues in the permissive environment created by the system, while external influences are restricted. Chondrocytes (cartilage cells) and osteoblasts (bone forming cells) develop to unite with the existing structure, so that after a period of time the implanted structure is virtually indistinguishable from the surrounding material.

Numerous advantages are derived from this approach in repair of articular cartilage, in comparison, for example, to replacement of a hip joint with a low friction plastic prosthesis. Implantation of a prosthesis disables the mechanoreceptor system in the capsule of the joint which provides feedback for muscle control, resulting in wear and ultimately a need for replacement. The multiple freedoms of motion required of the joint, as for rotational and sliding movement, cannot be provided because of the absence of the mechanoreceptor system. In addition, the best low friction plastics have over 100 times the friction of the natural cartilage structure with the intervening synovial fluid, and for this reason also wear and degradation are inevitable.

While the composition of U.S. Pat. No. 4,642,120 has a demonstrated potential for repair of articular cartilage, it also has been recognized to have a number of limitations as a result of further experimental work. The needed cell proliferation capability was thought to be best available in embryonal chondrocytes (young committed chondrocytes) but for human use availability is limited and major problems can arise from immune system reactions. Bone marrow stem cells are merely mentioned in the patent as a different possible source of cells, along with mesenchyme cells having potentiality for conversion to cartilage cells by self differentiation or under the direction of chondrogenic factors. No work was done using these progenitors. Additional detailed information and discussion is contained in an article entitled "Use of Cultured Chick Epiphyseal Chondrocytes as Grafts for Defects in Chick Articular Cartilage", by S. Itay et al, Clinical Orthopedics, pp. 284-302, July, 1987.

The article mentioned cites a number of articles of general relevance to the topic as a whole. Three of these are of particular interest because they evidence attempts to transplant chondrocytes into articular cartilage that encountered limited success because, at least in part, of the absence of suitable biodegradable viscoelastic material and inability to produce cartilage. These articles comprise: Bentley, G. et al, "Homotransplantation of isolated epiphyseal and articular cartilage chondrocytes onto joint surfaces of rabbits", *Nature* 230:385 (1971); Bentley, G. et al, "Isolated Epiphyseal chondrocyte allograft onto joint surface--An experimental study in rabbits", *Ann. Rheum. Dis.* 37:449 (1978); Helbing, G. et al, "In vitro Untersuchungen an isolierten Chondrozyten zur Prognose von Knorpeltransplanten", *Helv. Chir. Acta* 46:21 (1979).

As pointed out in U.S. Pat. No. 4,642,120, it was previously thought that a limit had to be observed for chondrocyte concentrations of about 500,000 cells per milliliter of gel in order to avoid necrosis of the cells. Also, it was thought that only 5-50 units of thrombin per milliliter and about 25-80 mg/ml fibrinogen should be employed, with the setting of the gel being determined by the level of the thrombin, which would be kept at a limit of less than 50 units/ml. These relationships and parameters were found on further studies to limit proliferation rates and capacities, and capability for maturation and transformation of the implant into suitable phenotypic expressions, especially in large defects. Consequently extension of this approach to repair of articular cartilage necessitates new compositions and procedures.

SUMMARY OF THE INVENTION

Compositions in accordance with the invention for regeneration of skeletal tissue employ cell cultures providing cells expressing a chondrogenic phenotype. Growth factors, mainly in the form of 15-20% serum, are employed to facilitate cell proliferation during this interval. A biological resorbable immobilization vehicle (BRIV) in the comprises about 15-30% serum, 100-150 mg/ml of fibrinogen, 60-90 units/ml thrombin, 60 mM $CaCl_2$, and 2000 units/ml (KIU) aprotonin. The cells in the implant are in the concentration of 80-160 $\times 10^6$ cells/ml in the BRIV. The resultant composition enables cell proliferation at a higher rate *in vivo*, matures more quickly and transforms more readily into histological identity with surrounding cartilage and bone structures.

Bone marrow progenital cells are the preferred progenitors, but embryonal cells and mesenchyme originated cells can also be used. The bone marrow progenital cells afford the advantage that the patient himself can be the donor at a convenient early time. The biological implant can be preserved by cryopreservation awaiting surgery. At the time of implantation the viscoelastic implant is thawed and the site is prepared.

In a preferred example representative values of chondrocytes concentrations are 32-120 $\times 10^6$ cells/ml of implant, together with about 90 units of thrombin per milliliter in 60 mM (milliMolar) of $CaCl_2$, 150 mg/ml fibrinogen, and 20% fetal calf serum. Generally a natural non-plasma proteinase inhibitor is used to prevent fast lysis of the matrix. A combination of polysaccharide inhibitors with plasma proteinase inhibitors and/or synthetic protease inhibitors can be used.

DETAILED DESCRIPTION OF THE INVENTION

EXAMPLE 1

Implant Containing Bone Marrow Derived Chondrocytes

Autologous or homologous bone marrow is obtained by aspiration with a bone biopsy needle from the iliac crest or femoral canal. The aspirated cells are injected into a phosphate buffered saline (PBS) containing 0.25% trypsin and injected sequentially through 17, 18 and 20 gauge needles to achieve a single cell suspension. Higher gauge needles are found to induce some cell destruction. The cells are plated in a density of 50–100 $\times 10^6$ cells on 100 mm tissue culture dishes fed with $BGJ_b$ medium (GIBCO) with 15% F.C.S. (Fetal Calf Serum). The medium is changed daily or as required by the proliferation rate of the cells. The medium may be supplemented by growth factors such as $IGF_I$, $IGF_{II}$, TGFB, PDGF or any other growth factors that will be found to facilitate the proliferation of the cells. The cells are subcultured weekly and after 5–6 subculturings an almost pure fibroblastic stromal cell population is achieved. This cell population is then trypsinized and put in a suspension culture at a density of 3–8 $\times 10^6$ cells/ml of medium and cultured above soft agar in a F-12 medium with 10% F.C.S. and 50 $\mu$gm/ml sodium ascorbate added daily to the medium. The fibroblastic stromal cells start to aggregate immediately and after three-seven days most of the cells are in aggregates of 30–60 cells. All the aggregates express a chondrogenic phenotype, as determined by employing histochemical and immunohistochemical probes for analysis.

Although bone marrow derived chondrocytes are preferred in this example, one can use chondrocytes or osteoblasts of autologous or homologous origin, or homologous committed chondrocytes, or any other progenital cells of mesenchymal origin. It can be seen that this initial formulation comprises purification, proliferation and manipulation of a population expressing a chondrogenic or osteogenic phenotype. More specifically, the proliferating cells are from the class comprising bone marrow stroma cells, embryonal committed chondrocytes and any undifferentiated mesenchymal cells.

To incorporate the cells in a biodegradable viscoelastic matrix the resulting pellet of cells is resuspended in a small volume of phosphate buffer saline containing fibrinogen (150 mg/ml) and 20% of fetal calf serum and aprotonin, available under the trademark "Trasylol" (2000 KIU/ml) or another antiprotease. The solution contains cells (ranging in concentration between 80–160 $\times 10^6$ cells/ml), fibrinogen, 15–30% serum and antiprotease and may be designated as solution A. Specifically in this example 120 $\times 10^6$ cells/ml of BRIV, 20% fetal calf serum, 150 mg/ml fibrinogen, 90 units/ml of thrombin in 60 mM $CaCl_2$, and 2,000 units of aprotonin are employed. A second solution, designated as solution B, comprises thrombin (b 90 units/ml in 60 mM $CaCl_2$). The solutions are mixed, keeping the ratio of solutions A and B 3:1 (v/v). The implant is immersed in F-12 medium containing 10% F.C.S. and may be immediately used. Alternatively the implant may be cryopreserved (in $LN_2$, for example) in 90% F.C.S. and 10% DMSO (or any other cryopreservation regime). At transplantation, the defect is sprayed with a thrombin solution and the implant is press fitted into the defect.

Data collected in experimentation with bone marrow derived chondrocytes and embryonal derived chondrocytes in several species (avian and mammalian) by macroscopic observation, histological sections, and biochemical test showed that at the site of transplantation within two months the defect is filled properly with a complete congruency at the articular surface and perfect integration with no fibrocartilage or other soft tissue at the interfaces. At 2 to 6 months all the implant that is below the osteochondral junction is transformed into bone while articular cartilage retains its cartilagenous properties. No degenerative changes or immunological rejection is observed after prolonged follow-up periods.

Although the serum is preferentially fetal calf serum in this example, umbilical cord serum from the second trimester or horse serum or any combination of these may be employed. No extracellular matrix need be used.

EXAMPLE 2

Preparation of Composition for Cartilage Repair

As starting material there were used epiphysis of long bones (tibia, femur, humerus). The isolation procedure of embryonal chondrocytes comprises trypsinization of the epiphysis (1% porcine trypsin), incubation for 60 minutes at 37° C. and vortexing for 2 minutes in each 10 minute interval and thereafter a gentle mechanical disintegration of the tissue by a Teflon channeled homogenizer. Trypsin activity terminated by serum which contains antiproteolytic substance. The resulting single cell suspension is then seeded for several days (4–7 days) in Ham F-12 medium on plates coated with soft agar (0.5% Bacto-agar in Ham F-12) at a density of 2 $\times 10^5$ to 4 $\times 10^5$ cells/ml. An amount of 50 $\mu$gr of sodium ascorbate is added daily to the medium. During this growth period most of the fibroblasts are dying off and chondrocyte enrichment does occur. The cells are collected by centrifugation and used directly or cryopreserved (90% fetal calf serum (F.C.S.) and 10% Dimethyl sulfoxide (DMSO) in liquid nitrogen for longer periods. The cells were collected and embedded in the same viscoelastic biodegradable matrix as in Example 1.

EXAMPLE 3

Preparation of Composition for Bone Repair

In order to regenerate bone defects one of three methods may be used.

3A. For small defects 2–4 cm in length one uses an implant as proposed in Example 1 or Example 2.

3B. For large defects a composition graft of bone substitute used as a supporting matrix with biomechanical properties near to the properties of a native bone is used. The cells are combined to this matrix via the biodegradable fibrinogen based adhesive matrix.

3C. The bone marrow stromal cells can be induced in vitro to express as osteoblastic phenotype and used directly as in 3A or 3B to correct bony defects. (This can be used only in the autologous group where the bone marrow originates from the patient with the bone defect.)

THE PROCESS

A traumatic (fracture) or pathologic (tumor) or degenerative disease defect in bone or articular cartilage is cleaned up and shaped into a geometric configuration (cuboidal or cylindrical). In the case of an articular surface all the procedure can be done through an arthroscopic device.

After the damaged area is prepared a frozen implant with an identical shape (prepared as described in detail in Example 1 or Example 2) is rapidly thawed by putting it into saline at 37° C. for 5-10 minutes.

The implant is then immersed in a solution of fibrinogen and the implantation site is sprayed with the thrombin solution. The implant is now press fitted into the defect. In an articular defect, continuous passive motion is started immediately.

In the case of large defects a composite graft of the biological implant embedded in (or above) a bone substitute material of suitable shape can be used. This implant will be either custom made or as a commercial standard type.

While various alternatives and modifications are proposed above, it will be appreciated that the invention is not limited thereto but encompasses all forms and variations in accordance with the appended claims.

I claim:

1. A method of comparing a skeletal tissue implant comprising the step of:

purification, proliferation and manipulation of a cell population expressing a specific chondrogenic or osteogenic phenotype, the proliferating cells being selected from the class consisting of bone marrow stroma cells, embryonal committed chondrocytes, and any undifferentiated mesenchymal cells and being concentrated to between $80 \times 10^6$ and $160 \times 10^6$ cells/ml; and embedding the cells in a biological resorbable immobilization vehicle (BRIV) comprising at least 15-14 30% serum, 100-150 mg/ml fibrinogen, and 60-90 units/ml thrombin, and wherein the BRIV further includes about 2,000 units/ml aprotonin.

* * * * *

UNITED STATES PATENT AND TRADEMARK OFFICE
CERTIFICATE OF CORRECTION

PATENT NO. : 5,053,050
DATED : October 1, 1991
INVENTOR(S) : Samuel Itay

It is certified that error appears in the above-identified patent and that said Letters Patent is hereby corrected as shown below:

Column 2, line 39, insert --composition-- after the word "the".

Column 3, line 54, "106" should read --$10^6$--.

Column 3, line 56, "106" should read --$10^6$--.

Column 3, line 60, delete "b" after the word "thrombin (".

Column 4, line 30, insert --is-- after the word "activity".

Column 4, line 34, "105" should read --$10^5$--.

Column 4, line 35, "105" should read --$10^5$--.

Column 6, line 4, "comparing" should read --preparing--.

Column 6, lines 15-16, "15-14 30%" should read --15-30%--.

Signed and Sealed this

Sixteenth Day of March, 1993

Attest:

STEPHEN G. KUNIN

Attesting Officer

Acting Commissioner of Patents and Trademarks